(12) United States Patent
Baumann et al.

(10) Patent No.: US 6,807,445 B2
(45) Date of Patent: Oct. 19, 2004

(54) TOTALLY IMPLANTABLE HEARING SYSTEM

(75) Inventors: Joachim W. Baumann, Markt Schwaben (DE); Hans Leysieffer, Taufkirchen (DE)

(73) Assignee: Cochlear Limited, Lane Cove (AU)

( * ) Notice: Subject to any disclaimer, the term of this patent is extended or adjusted under 35 U.S.C. 154(b) by 406 days.

(21) Appl. No.: 10/101,054

(22) Filed: Mar. 20, 2002

(65) Prior Publication Data

US 2002/0138115 A1 Sep. 26, 2002

(30) Foreign Application Priority Data

Mar. 26, 2001 (DE) .......................................... 101 14 838

(51) Int. Cl.[7] .............................................. A61N 1/18
(52) U.S. Cl. ...................................................... 607/57
(58) Field of Search ..................... 607/55–57; 381/312, 381/316, 326, 385; 341/132; 600/25, 559; 73/585

(56) References Cited

U.S. PATENT DOCUMENTS

| | | | |
|---|---|---|---|
| 4,485,276 A | * 11/1984 | Sato | ........................... 381/385 |
| 4,816,125 A | 3/1989 | Muller et al. | |
| 4,998,179 A | 3/1991 | Grantham et al. | |
| 5,277,694 A | 1/1994 | Leysieffer et al. | |
| 5,279,292 A | 1/1994 | Baumann et al. | |
| 5,663,727 A | * 9/1997 | Vokac | ........................ 341/132 |
| 5,814,095 A | 9/1998 | Müller et al. | |
| 5,941,814 A | 8/1999 | Lehner et al. | |
| 5,999,632 A | 12/1999 | Leysieffer et al. | |
| 6,077,215 A | 6/2000 | Leysieffer | |
| 6,123,660 A | 9/2000 | Leysieffer | |
| 6,162,169 A | 12/2000 | Leysieffer | |
| 6,198,971 B1 | 3/2001 | Leysieffer | |

FOREIGN PATENT DOCUMENTS

| | | |
|---|---|---|
| EP | 0 683 621 A2 | 11/1995 |
| EP | 0 831 674 A2 | 3/1998 |
| EP | 1 043 914 A2 | 3/2001 |
| WO | WO 00/69215 | 11/2000 |

OTHER PUBLICATIONS

Leysieffer et al., "A Totally Implantable Hearing Device for the Treatment of Sensorineural Hearing Loss: TICA LZ 3001", pp. 853–863, 1998, HNO vol. 46.

Zenner et al., "First Implantations of a Totally Implantable Electronic Hearing System for Sensorineural Hearing Loss", pp. 844–852, 1998, HNO vol. 46.

Zenner et al., "Totally Implantable Hearing Device for Sensorineural Hearing Loss", p. 1751, 1998, The Lancet vol. 352, No. 9142.

European Search Report Dated Nov. 28, 2003.

* cited by examiner

*Primary Examiner*—George Manuel
(74) *Attorney, Agent, or Firm*—Nixon Peabody LLP; David S. Safran

(57) ABSTRACT

A totally implantable hearing system for rehabilitation of hearing disorders, comprising at least one implantable sensor for picking up at least airborne sound and for converting it into electrical airborne sound signals, and at least one implantable sensor for picking up at least body sound-induced signals and for converting them into electrical body sound signals. The hearing system further comprises an electronic module including electronic means for processing and amplification of said airborne sound signals and said body sound signals. The electronic means include means for individually adjusting the ratio of airborne sound signals to body sound signals. The hearing system also comprises an output-side actuator arrangement for stimulation of the middle or inner ear, and an electrical power supply unit which supplies individual components of the system with energy.

43 Claims, 11 Drawing Sheets

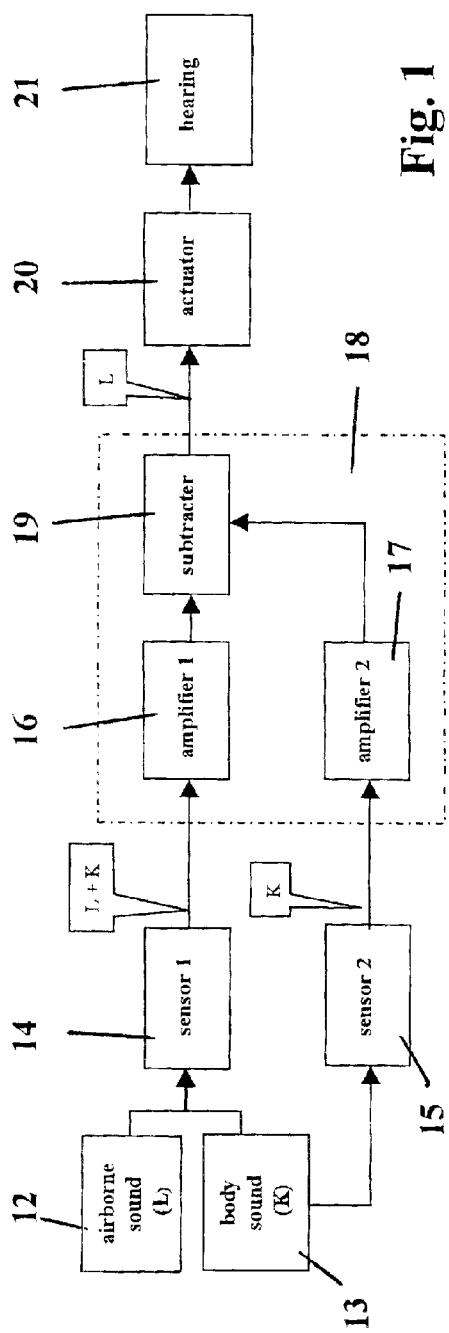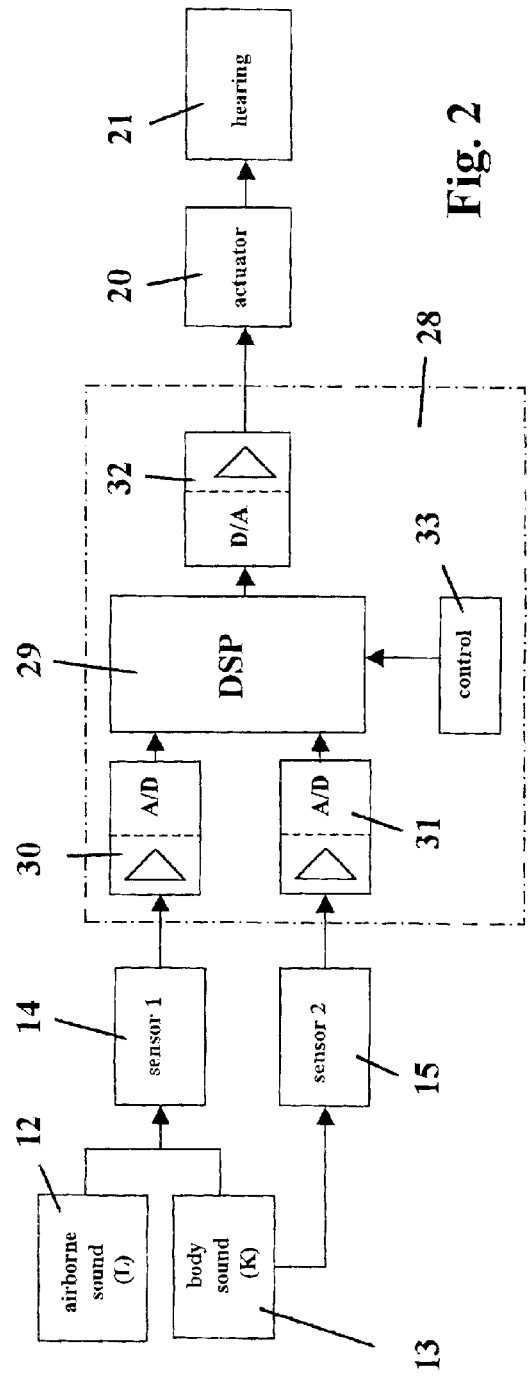

TOTALLY IMPLANTABLE HEARING SYSTEM

BACKGROUND OF THE INVENTION

1. Field of the Invention

This invention relates to a totally implantable hearing system for rehabilitation of hearing disorders, comprising at least one sensor for picking up at least airborne sound and converting it into electrical signals, an electronic module including electronic means for audio signal processing and amplification, an output-side actuator arrangement for stimulation of the middle or inner ear, and an electrical power supply unit.

2. Description of Related Art

The expression "hearing disorder" is defined here as including all types of inner ear damages up to complete postlingual loss of hearing or prelingual deafness, combined inner ear and middle ear damages, and temporary or permanent noise impressions (tinnitus).

In recent years, rehabilitation of sensorineural hearing disorders with partially implantable electronic systems has acquired major importance. In particular, this applies to the group of patients in which hearing has completely failed due to accident, illness or other effects or in which hearing is congenitally non-functional. If, in these cases, only the inner ear (cochlea), and not the neural auditory path which leads to the brain, is affected, the remaining auditory nerve can be stimulated with electrical stimulation signals. Thus, a hearing impression can be produced which can lead to speech comprehension. In these so-called cochlear implants (CI), an array of stimulation electrodes is inserted into the cochlea. This array is controlled by an electronic system which is surgically embedded as a hermetically sealed, biocompatibly encapsulated electronic module in the bony area behind the ear (mastoid). The electronic system contains essentially only decoder and driver circuits for the stimulation electrodes. Acoustic sound reception, conversion of this acoustic signal into electrical signals and further processing of the latter, always takes place externally in a so-called speech processor which is worn outside on the body. The speech processor superimposes the preprocessed signals, properly coded, on a high frequency carrier signal which, via inductive coupling, is transmitted (transcutaneously) to the implant through the closed skin. The sound-receiving microphone is always located outside of the body and, in most applications, in a housing of a behind-the-ear hearing aid worn on the external ear. The microphone is connected to the speech processor by a cable.

In addition to rehabilitation of congenitally deaf persons and those who have lost their hearing using cochlear implants, for some time there have been approaches to offer better rehabilitation than with conventional hearing aids by using partially or totally implantable hearing aids for patients with a sensorineural hearing disorder which cannot be surgically corrected. The principle consists, in most embodiments, in stimulating an ossicle of the middle ear or, directly, the inner ear via mechanical or hydromechanical stimulation and not via the amplified acoustic signal of a conventional hearing aid in which the amplified acoustic signal is supplied to the external auditory canal. The actuator stimulus of these electromechanical systems is accomplished with different physical transducer principles such as, for example, by electromagnetic and piezoelectric systems. The advantage of these devices is seen mainly in a sound quality which is improved compared to that of conventional hearing aids, and, for totally implanted systems, in the fact that the hearing prosthesis is not visible. Such partially and totally implantable electromechanical hearing aids are described, for example, by H. P. Zenner et al. "First implantations of a totally implantable electronic hearing system for sensorineural hearing loss", in HNO Vol. 46, 1998, pp. 844–852; H. Leysieffer et al. "A totally implantable hearing device for the treatment of sensorineural hearing loss: TICA LZ 3001", in HNO Vol. 46, 1998, pp. 853–863; and H. P. Zenner et al. "Totally implantable hearing device for sensorineural hearing loss", in The Lancet Vol. 352, No. 9142, page 1751.

Many patients with inner ear damage also suffer from temporary or permanent noise impressions (tinnitus) which cannot be surgically corrected and for which, to date, there are no approved drug treatments. Therefore, so-called tinnitus maskers have become known. These are small, battery-driven devices which are worn like a hearing aid behind or in the ear and which, by means of artificial sounds which are emitted, for example, via a hearing aid speaker into the auditory canal, psychoacoustically mask the tinnitus and thus reduce the disturbing noise impression, if possible, to below the threshold of perception. The artificial sounds are often narrow-band noise (for example, third-band noise). The spectral position and the loudness level of the noise can be adjusted via a programming device to enable adaptation to the individual tinnitus situation as optimally as possible. In addition, the so-called retraining method has been developed recently in which, by combination of a mental training program and presentation of broad-band sound (noise) near the auditory threshold, the perceptibility of the tinnitus in quiet conditions is likewise supposed to be largely suppressed. These devices are also called "noisers".

In the two aforementioned methods for hardware treatment of tinnitus, hearing aid-like, technical devices must be carried visibly outside on the body in the area of the ear. They stigmatize the wearer and, therefore, are not willingly worn.

Recently, partially and totally implantable hearing systems for rehabilitation of inner ear damage have been introduced in clinical use. In the case of the totally implantable hearing system TICA® (H. P. Zenner et al. ("Totally implantable hearing device for sensorineural hearing loss", The Lancet, Vol. 352, November 1998, No. 9142, page 1751) an audio sound sensor (microphone) is used which is subcutaneously inserted in the rear bony wall of the auditory canal as disclosed in more detail in U.S. Pat. Nos. 5,814,095 and 5,999,632. First clinical experiences with this system show that the own voice as well as other body sound vibrations, such as chewing and swallowing noise, are clearly and disturbingly loudly perceived by some patients. This is due to the fact that not only airborne signals incident from the exterior are picked up by the audio sensor, but also body sound-induced signals are acting on the audio sensor by bone transmission and, upon amplification by the implanted hearing system, likewise are transmitted to the inner ear. In view of this mixture of the individual input signal components the familiar and desirably natural sound pattern of the own voice changes in the case of these patients, or the amplified body sound portion is acting as interference which may be masking, whereby the hearing and understanding of external language is impeded. This effect cannot be countered in prior hearing implants because the implanted audio sensor and the input-side functioning thereof cannot be influenced. This disturbing effect likewise is to be expected in future totally implantable cochlea implants since it can impede the hearing rehabilitation required for such implants in a still more pronounced manner than in the case of electromechanical implants for patients with defective hearing. Perhaps, a way out would be an implantation of the audio sensor in a manner in which this sensor is completely decoupled from body sound, by using proper body sound-insulating implant materials and/or structural features in the audio sensor itself. At least theoretically the described negative effect would be eliminated thereby. However, all body sound-induced components of the own voice, such as particularly mechanical laryngeal oscillations which are indispensable for a familiar, natural sound pattern of the own voice, likewise are suppressed thereby.

SUMMARY OF THE INVENTION

In order to increase the acceptance of totally implantable hearing systems using actoric output stimuli of any type, a technical solution of the above problems is desirable. Accordingly, a primary object of the present invention is to devise a hearing system which individually on the one hand prevents an unwanted amplification of body sound-induced signals and which on the other hand permits the transmission of such a part of these signals that a comfortable and natural hearing impression, particularly of the own voice, is attained.

In conformity with the subject invention a totally implantable hearing system for rehabilitation of hearing disorders, comprises:

at least one implantable sensor for picking up at least airborne sound and for converting it into electrical airborne sound signals;

at least one implantable sensor for picking up at least body sound-induced signals and for converting them into electrical body sound signals;

an electronic module including electronic means for processing and amplification of said airborne sound signals and said body sound signals, said electronic means including means for individually adjusting the ratio of airborne sound signals to body sound signals;

an output-side actuator arrangement for stimulation of the middle or inner ear; and an electrical power supply unit which supplies individual components of the system with energy.

Particularly, the ratio of airborne sound signals to body sound signals may be adjusted such that, upon further signal processing and passing of the signals to the output-side actuator arrangement, a hearing impression, especially of the own voice, can be generated which is well-balanced between external airborne sound signals and endogenuos sound signals.

The body sound sensor or sensors is (are) preferably localized in the bony part of the skull. The sensor, for example, may be arranged separate from the electronic module and may be fixedly or detachably connected therewith e.g. by a separable plug-type connector. An advantageous implantation site is the bony part of the mastoid behind the outer ear. In this embodiment, the sensor is disposed within a hermetically sealed housing having a biocompatible surface, and the housing preferably is directly fixedly attached, e.g. by screws, to the bone at the application site in order to provide for a particularly good transmission of body sound.

The body sound sensor, however, also may be disposed in the same housing as the sensor for airborne sound provided that it is in mechanical contact with bony parts of the skull, such as for example the microphone known from commonly owned U.S. Pat. Nos. 5,814,095 and 5,999,632 which hereby are incorporated by reference. Another advantageous application site for the body sound sensor or sensors is within the housing of the electronic module of the implant. In the case of implantable hearing systems this housing basically is imbedded in the bone of the mastoid, so that a proper transmission of body sound is to be expected. A further advantage of the two last-mentioned embodiments is that in such a case the body sound sensor itself needs not to be hermetically sealed and biocompatible as this is required in the first mentioned embodiment in which the body sound sensor is separately applied in an own housing.

The at least one body sound sensor may utilize any known electromechanical transducer principle; preferably it is an electromagnetic, electrodynamic, piezoelectric, magnetostrictive or dielectric (capacitive) sensor. In a manner known per se from U.S. Pat. Nos. 4,816,125 and 4,998,179 the body sound sensor may be an on-chip semiconductor transducer. Preferably, the body sound sensor is operating in conformity with the known principle of an acceleration pick-up, wherein a mechanical-electrical transducer is coupled within the sensor housing to an inert (seismic) mass suspended for oscillating. Preferably, a piezoelectric element is used as mechanical-electrical transducer. A body sound sensor in the form of an on-chip semiconductor transducer advantageously may be integrated into a semiconductor component of the electronic module or of an airborne sound sensor module. Furthermore, commercial, body sound-sensitive, capacitive electret microphones of the conventional hearing device industry may be used. The latter embodiments are advantageous in that they may be miniaturized what favors the insertion of the hearing implant in the head region.

The spectral transmission range of the body sound sensors is in the audio range, preferably from about 100 Hz to about 10 kHz. Advantageously, the sensors are tuned to have a first mechanical resonant frequency at the upper end of the desired transmission frequency range. Thereby the transducer frequency characteristic of the sensors is essentially free from resonances and thus shows very low ripple.

The ratio of airborne sound signals to body sound signals may be adjusted in any desired manner, for example by using telemetry means which permit the transmission of data between an external unit and the implant, or, in the case of a highly intelligent implant system, by the implant reacting on corresponding speech signals of the implant wearer.

The further electronic processing of the airborne sound signals and the body sound signals may be effected via analog preamplifiers and analog or—after a corresponding analog-to-digital conversion—digital signal processing, wherein processing of the sensor signals is effected in the signal processing unit in a manner taking into consideration both amplitude and phase signals, so that possibly required corrections of various phase and group delays can be made. After spectral filtering, such a signal processing also can be carried out in a plurality of frequency bands. The respective signal processing parameters can be electronically stored within the implant and preferably can be adapted from the outside via a interface of the implant to thus arrive for the individual patient—after implantation, a telemetry healing period and first hearing experiences—at an optimum rehabilitation result by iterative programming of these parameters.

Preferably, processing of the sensor signals is effected in a purely digital manner in a digital signal processor the software operating system of which or parts of this software operating system being adapted to be telemetrically charged or changed as described in more detail in commonly owned U.S. Pat. No. 6,198,971 which hereby is incorporated by reference. Thereby, with progress in scientific knowledge or field experiences, always an optimum signal processing algorithm may be offered to the patient without the need to exchange the implant.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIG. 1 is a block diagram of a totally implantable hearing system with analog signal processing for rehabilitation of a middle and/or inner ear disorder and/or of a tinnitus FIG. 2 is a block diagram of a totally implantable hearing system with digital signal processing for rehabilitation of a middle and/or inner ear disorder and/or of a tinnitus

DETAILED DESCRIPTION OF THE INVENTION

Figure 3:
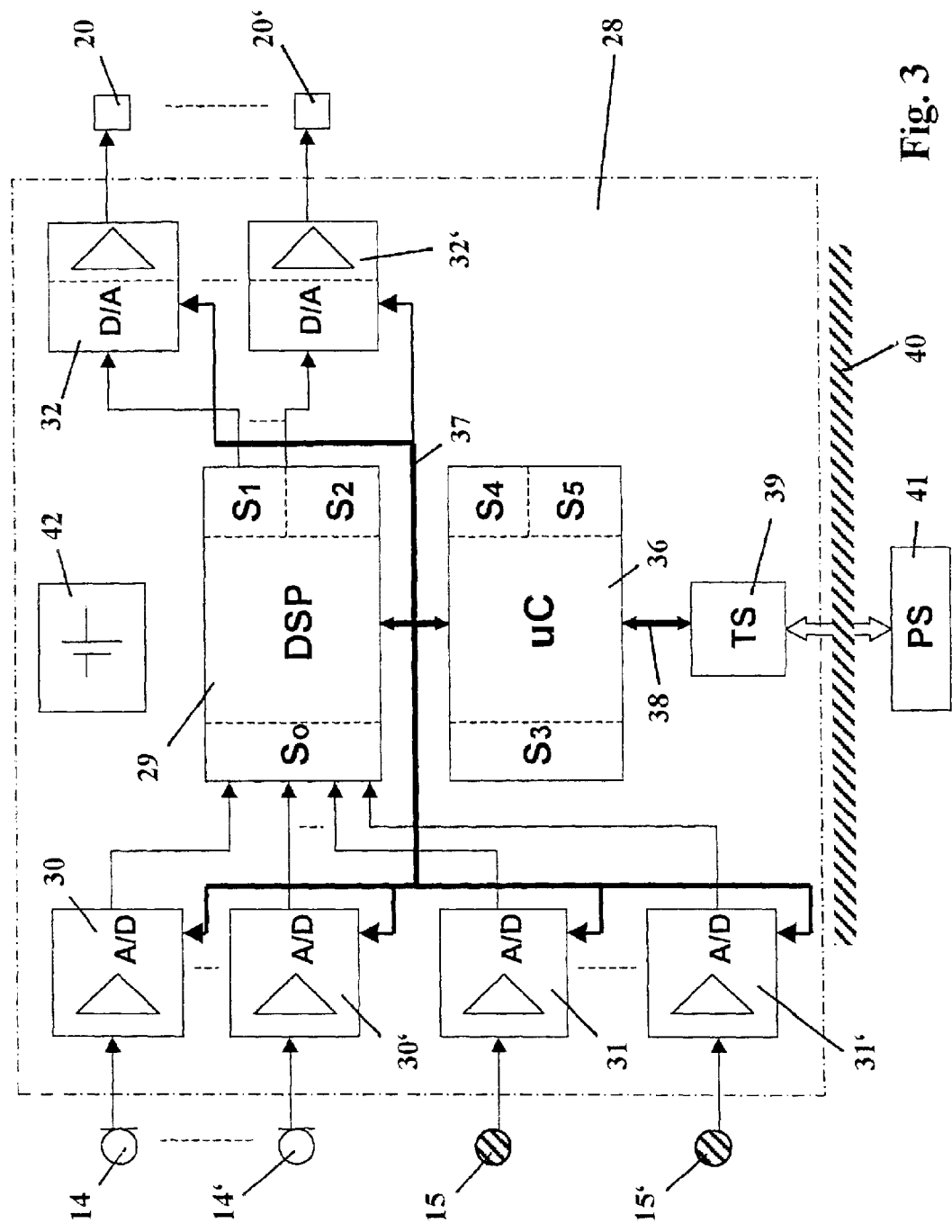
FIG. 3 is a block diagram of a further embodiment of a totally implantable hearing system with digital signal processing for rehabilitation of a middle and/or inner ear disorder and/or of a tinnitus.

In the block diagram of a totally implantable hearing system shown in FIG. 1 externally incident airborne sound (L) and body sound (K) occurring in the implanted state internally of the implant bearer are indicated by blocks 12 and 13, respectively. The hearing system comprises a microphone in form of a sensor 14 which picks up both airborne sound and body sound (indicated in FIG. 1 as "L+K"). The hearing system also includes a further sensor 15 which is designed and arranged to pick up in the implanted state essentially body sound only. Sensors 14, 15 convert the incident sound into corresponding electrical signals. Amplifiers 16 and 17, respectively, provided in an electronic module 18, are connected to outputs of sensors 14, 15. Amplifiers 16, 17 provide for an amplification of the respective electrical sensor signal delivered by sensor 14 and 15, respectively. The output signals of amplifiers 16, 17 are applied to a subtracter 19 which produces a signal corresponding to the difference of the two weighted sensor signals, wherein a proper weighting of the electrical sensor signals is provided for. In an extreme case this can result in that merely the airborne sound signal L is passed from subtracter 19 to an implant-specific actuator arrangement 20 and thus to a damaged hearing 21. As indicated above, subtracter 19 is adapted to process amplitude and phase information in a spectrally weighted manner, so that by adjusting these parameters (not illustrated) any desired, individually adjustable mixture of the signals L and K may be passed to the hearing FIG. 2 shows a preferred embodiment of a totally implantable hearing system provided with an electronic module 28 having a digital signal processor (DSP) 29. Electronic module 28 further includes A-D converter units 30 and 31 connected between the outputs of sensors 14, 15 and inputs of the signal processor 29, and a D-A converter unit 32 connected between an output of signal processor 29 and an input of actuator arrangement 20. The A-D converter units 30 and 31 provide for an amplification and A-D conversion of the analog sensor signals. The sensor signals, upon conversion thereof into digital signals, are processed in the indicated manner in the digital signal processor 29, wherein signal processor 29 also provides for the audiologic signal processing of the respective implant system. The digital output signal (or signals) of signal processor 29 is reconverted in the D-A converter unit 32 into an analog signal and, upon amplification in a driver adapted to the respective type of stimulation of the implant system, is passed to the output-side actuator arrangement 20 which is illustrated in FIG. 2 in single-channel form only. A control unit 33 is associated to signal processor 29.

FIG. 3 shows details of a preferred structure of the electronic signal processing module 28 of FIG. 2. The external airborne sound and internal body sound signals are picked up by one or more microphones (sensors) 14, 14' and are converted into corresponding electrical signals. These sensor signals are routed to A-D converter units 30, 30' in which they are preamplified and converted into digital signals (A/D). One or more further sensors 15, 15' pick up the internal body sound. These sensor signals likewise are preamplified and converted into digital signals in A-D converter units 31, 31'. All the digitized sensor signals are further processed in the digital signal processor (DSP) 29.

The signal processor 29 contains a read-only-memory area $S_0$ which cannot be overwritten and in which the instructions and parameters necessary for "minimum operation" the system are stored, and at least one storage area $S_1$ which can be repeatedly overwritten and in which the operating software of the intended function or functions of the implant system are stored. Preferably, this storage area is provided twice ($S_1$ and $S_2$). The rewriteable program storage for storing the operating software can be based on EEPROM or on static RAM cells, and, in the latter case, provisions should be made for this RAM area to always be "buffered" the power supply system within the implant. Patient-specific data which may be altered from the exterior, such as audiologic adaptation parameters, likewise may be stored in the storages $S_1$ and/or $S_2$.

The digital output signals of the signal processor 29 are converted in the digital-analog converter units (D/A) 32, 32' into analog signals and are amplified to the level desired for controlling the actuator arrangements 20, 20'. The actuator output side of the implant system may be defined by one or more electromechanical or electroacoustical transducers or by electrical stimulation electrodes or by any desired combination of such output stimulators. Units 32, 32' can optionally be omitted, if, for example, in a hearing system comprising an electromagnetic intracochlear output transducer, for example, a pulse-width modulated, serial digital output signal of signal processor 29 is transferred directly to the actuator or actuators 20, 20'.

The system as shown in FIG. 3 contains a further microprocessor module, for example, a microcontroller ($\mu$C) 36, in order to permit the software-based algorithms for as optimum as possible simulation of the cochlear amplifier to be implemented also postoperatively. Microcontroller 36 controls the A-D converters of the sensor-preprocessor units 30, 30', 31, 31', the D-A converter of the units 32, 32' for controlling the actuators 20, 20' as well as the signal processor 29 itself via a data bus 37, and for this purpose includes one or two associated storages $S_4$ and $S_5$, respectively. Especially, operating software portions of an implant management system (for example, administration, monitoring and telemetry functions) may be stored in the storage areas $S_4$ and $S_5$. Microcontroller 36 furthermore includes a rewriteable storage $S_3$ is in which an operating program for the microcontroller 36 is stored.

The microcontroller 36 communicates via a data bus 38 with a telemetry system (TS) 39. Telemetry system 39 in turn wirelessly communicates in bidirectional manner, for example, via inductive coupling, through the closed skin indicated at 40 with an external programming system (PS) 41. The programming system 41 can be a PC-based system with corresponding programming, processing, display and administration software. Via this telemetry interface, the operating software of the implant system which is to be changed or completely replaced is transmitted and at first buffered in the storage area $S_4$ and/or $S_5$ of the microcontroller 36. Thus, for example, storage area $S_5$ may be used for a complementary storing of the data transmitted from the external system, and simple verification of software transmission can be done by a reading process via the telemetry interface to check coincidence of the contents of the storage areas $S_4$ and $S_5$ before the content of rewriteable storage $S_3$ is changed or replaced.

The operating software of the implantable hearing system is considered in the present context to include the operating software of microcontroller 36 (for example house keeping functions, such as energy management or telemetry functions) as well as the operating software of the digital signal processor 29. Thus, for example, a simple verification of software transmission may be effected by a reading process via the telemetry interface before the operating software or the corresponding signal processing parts of this software are transferred into the program storage area $S_1$ of the digital signal processor 29. Furthermore, the operating program for the microcontroller 36, which for example is stored in the repeatedly rewriteable storage $S_3$, also can be changed or replaced in whole or in part via the telemetry interface 39 using the external programming system 41.

On the other hand, the microcontroller 36 controls, via the bidirectional data bus 37, the A/D-converters 30, 30', 31, 31' of the sensor preprocessing unit, the D/A converters 32, 32' for controlling the output actuators 20, 20' and the signal processor 29 itself within the implant. Via the data bus 37, program parts or entire software modules are also transmitted between the outside world, the microcontroller 36 and the signal processor 29.

Electrical operating energy is supplied to all the electronic components of the implant system by a primary or secondary battery 42.

The described solution allows matching of the hearing system to circumstances which can be detected only after implantation. Thus, for example, in an implantable hearing system for rehabilitation of a monaural or binaural inner ear disorder and of a tinnitus by mechanical stimulation and/or electrical excitation of the inner ear, the sensoric (airborne sound and body sound sensors) and actoric (output stimulator) biological interfaces are always dependent on anatomic, biological and neurophysiological circumstances, for example on the interindividual healing process. These interface parameters can also be individual, also especially time-variant. Thus, for example the transmission behavior of an implanted airborne sound or body sound sensor can vary interindividually and individually as a result of being covered by tissue, and the transmission behavior of an electromechanical transducer which is coupled to the inner ear can vary in view of different coupling qualities. These differences of interface parameters, which normally cannot be eliminated or reduced even by replacing the implant, can be optimized in the subject hearing system by changing or improving the signal processing of the implant.

In an implantable hearing system, it also can be advisable or become necessary to implement signal processing algorithms which have been improved after implantation. Especially the following should be mentioned here.

processes for optimizing the ratio of airborne sound to body sound, speech analysis processes (for example, optimization of a fast Fourier transform (FFT)), static or adaptive noise detection processes, static or adaptive noise suppression processes, processes for optimization of the signal to noise ratio within the system, optimized signal processing strategies in progressive hearing disorder, output level-limiting processes for protection of the patient in case of implant malfunctions or external faulty programming, processes of preprocessing of several airborne sound and/or body sound signals, especially for binaural positioning of the sensors, processes for binaural processing of two or more airborne sound sensor signals in binaural sensor positioning, for example optimization of spacial hearing or spacial orientation, phase or group delay time optimization in binaural signal processing, processes for optimized driving of the output stimulators, especially for binaural positioning of the stimulators.

Among others, the following signal processing algorithms can be implemented with this system even after implantation:

processes for feedback suppression or reduction, processes for optimization of the operating behavior of the output transducer(s) (for example, optimization of the frequency response and phase response, improvement of the impulse response), speech signal compression processes for sensorineural hearing loss, signal processing methods for recruitment compensation in sensorineural hearing loss.

Furthermore, in implant systems with a secondary power supply unit, i.e., a rechargeable battery system, but also in systems with primary battery supply, it can be assumed that these electrical power storages will enable longer and longer service lives, and thus, increasing residence times in the patients as technology advances. It can also be assumed that fundamental and applied research for signal processing algorithms will make rapid progress. The necessity or the desire for operating software adaptation and modification will therefore presumably take place before the service life of the implanted power source expires. The system described here allows this adaptation of the operating programs of the implant even when it has already been implanted.

The respective signal-processing software modules of the digital signal processor 29 can be designed to be static or dynamic. "Static" presently is intended to mean that the software modules, as a result of scientific findings, are stored once in a program storage of the signal processor 29 and remain unchanged. On the other hand, "dynamic" presently is intended to mean that these software modules are able to "learn" to approximate the desired function by iteration. This means that the software modules may be designed to be adaptive, and that a parameter adaptation is effected through "training" by the wearer of the implant and optionally by further aids such as rehabilitation programs. Furthermore, a software module may be included which approximates an optimum hearing rehabilitation on the base of a neuronal network that is capable of being learned. This neuronal network again may be trained by the implant wearer and/or by using further external aids.

Figure 4:
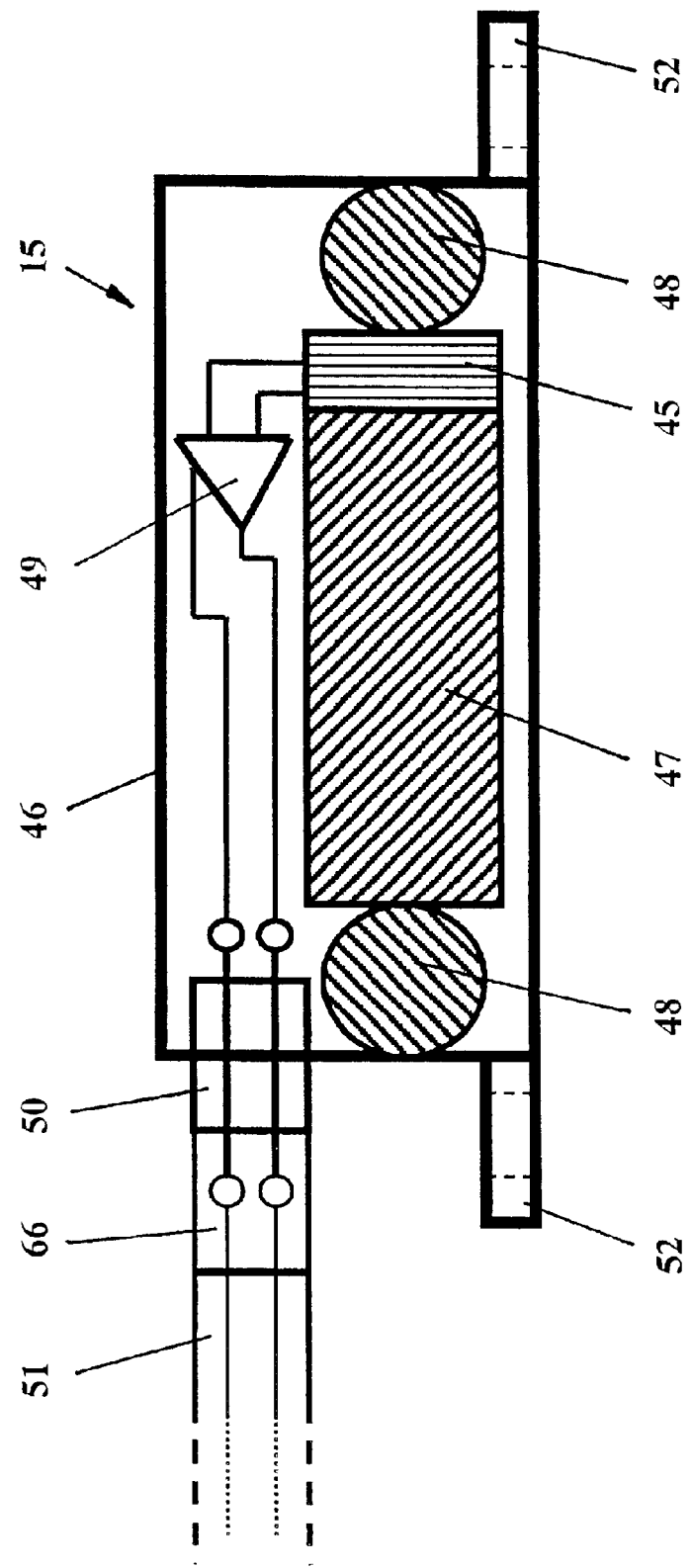
FIG. 4 is a schematic sectional view of a suitable body sound sensor.

FIG. 4 schematically shows an example of a separate body sound sensor 15 comprising a piezoelectric transducer element 45. An inert mass 47 is mechanically connected to the piezoelectric element 45 within a hermetically sealed and biocompatible housing 46. This compound is mounted in housing 46 via elastic members 48. Mechanical oscillations, such as body sound oscillations, acting on the housing 46 cause dynamic relative motions of the inert mass 47 and thus deflections of the piezoelectric element 45. The voltage signals of piezoelectric element 45 produced thereby are picked up via an impedance transformer and preamplifier unit 49 disposed within housing 46. The electrical sensor output signal is passed to the electronic module 18 or 28, respectively, of the implant system via hermetically sealed lead-through means 50 and an implant sensor line 51. When using a bipolar sensor line 51, the impedance transformer and preamplifier unit 49 may be supplied with energy by a phantom connection. Housing 46 is provided with a projecting flange 52 for fixing the body sound sensor 15, e.g. by means of screws.

Figure 5:
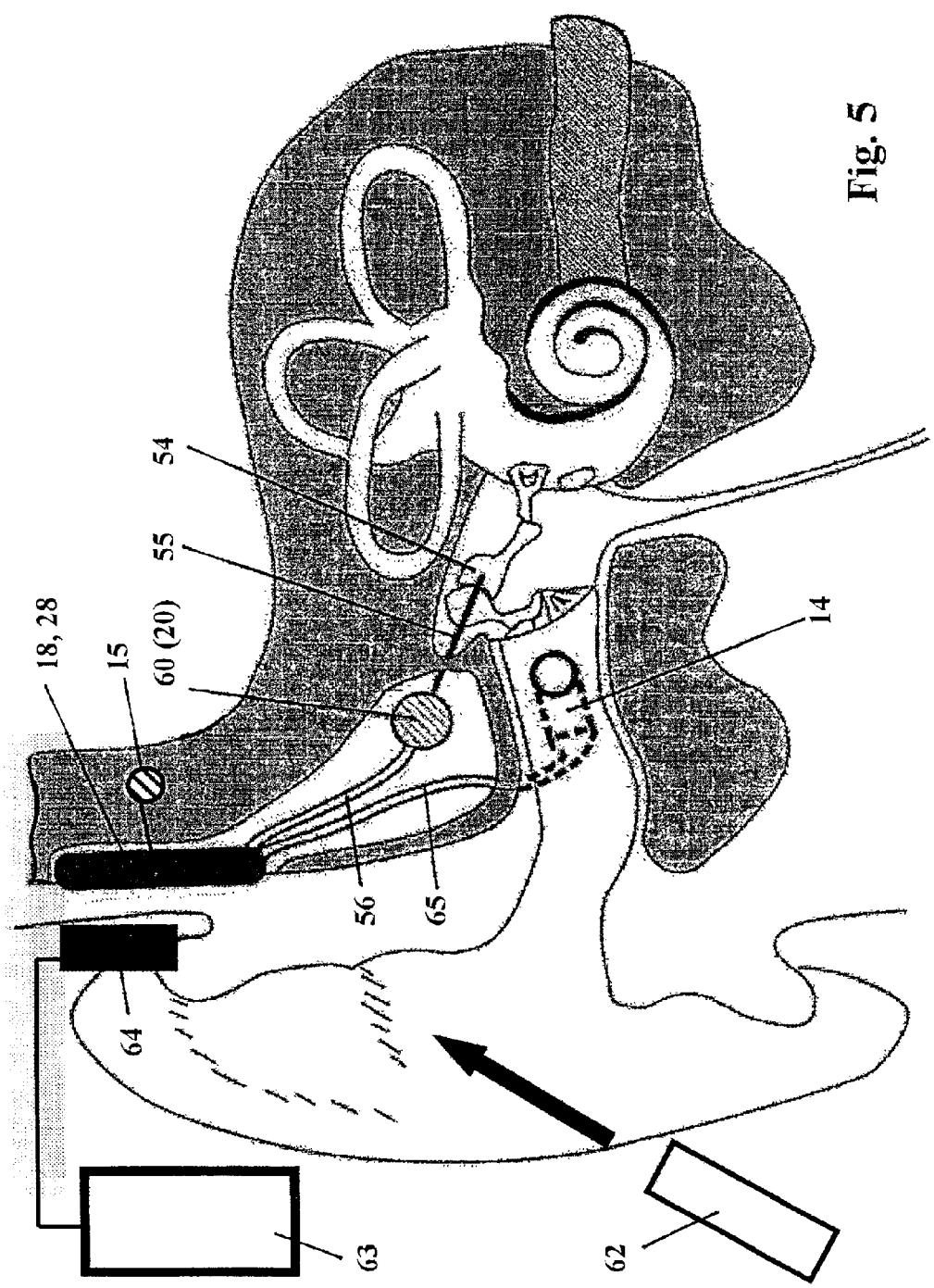
FIGS. 5 to 7 illustrate embodiments of totally implantable hearing systems in conformity with the subject invention with different arrangements of the body sound sensor and with single-channel electromechanical stimulation of the damaged inner ear by vibratory stimulation of the middle ear.

FIG. 5 schematically shows the structure of a completely implantable hearing system providing for single-channel electromechanical stimulation of the damaged inner ear by vibratory excitation of the middle ear, wherein, for example, an electromechanical transducer 60 which is coupled by a coupling rod 55 to an incus 54, is used as an output-side actuator (20 in FIGS. 1 to 3). Transducer 60 generally may be designed as any electromagnetic, electrodynamic, piezoelectric, magnetostrictive or dielectric (capacitive) transducer. Particularly suited is a piezoelectric transducer system of the type known from commonly owned U.S. Pat. No. 5,277,694 which is hereby incorporated by reference. Such a preferred transducer is provided with a biocompatible cylindrical housing of electrically conductive material, such as titanium. The housing is filled with an inert gas. An electrically conductive, preferably circular membrane that can oscillate, is disposed within the housing, with an outer edge of the membrane being fixedly connected to the housing. A thin disk of piezoelectric material, e.g. lead-zirconate-titanate, is in electrically conductive connection with one side of the membrane. The piezoelectric disk is contacted, at the side thereof remote from the membrane, with a thin flexible wire which is connected via a hermetically sealed housing lead-through connector to a transducer line 56. Application of an electrical voltage to transducer 60 results in a deformation of the hetero-compound consisting of membrane and piezoelectric disk. Such an electromechanical output transducer 60 typically has a relatively high mechanical output impedance, preferably a mechanical output impedance which is higher than the mechanical load impedance of the biological structure of the middle ear and/or the inner ear coupled to the transducer in the implanted state.

Transducer 60, which is merely schematically illustrated in FIG. 5, may also be modified in the manner explained in commonly owned U.S. Pat. No. 6,123,660, which is hereby incorporated by reference, such that a permanent magnet is attached at the side of the piezoelectric disk averted from the membrane, which permanent magnet cooperates with an electromagnetic coil in the manner of an electromagnetic transducer. Such a combined piezoelectric-electromagnetic transducer is of advantage particularly with respect to a broad frequency band and to attain relatively high oscillation amplitudes at relatively small amounts of supplied energy. The actuator 20 further may be an electromagnetic transducer of the type described in commonly owned U.S. Pat. No. 6,162,169 which likewise is hereby incorporated by reference.

To couple the electromechanical transducer 60 to the middle ear or the inner ear, especially coupling arrangements as described in commonly owned U.S. Pat. No. 5,941,814, which is hereby incorporated by reference, are suited in which a coupling element, in addition to a coupling part for the pertinent coupling site, has a crimp sleeve which is first slipped loosely onto a rod-shaped part of the coupling rod 55 connected to the transducer. This rod-shaped part of the coupling rod is provided with a rough surface. During implantation, the crimp sleeve can simply be pushed and turned relative to the coupling rod to exactly align the coupling part of the coupling element with the intended coupling site. Then, the crimp sleeve is fixed by being plastically cold-deformed by means of a crimping tool. Alternatively, the coupling element can be fixed with reference to the coupling rod by means of a belt loop which can be tightened.

Other coupling arrangements which can be preferably used here are described, in particular, in commonly owned, co-pending U.S. patent application Ser. Nos. 09/576,009, 09/626,745, 09/613,560, 09/680,489 and 09/680,488, all of which hereby are incorporated by reference. Thus, according to commonly owned, co-pending U.S. patent application Ser. No. 09/576,009, a coupling element can have a contact surface on its coupling end which has a surface shape which is matched to or can be matched to the surface shape of the coupling site, and has a surface composition and surface size such that, by placing the coupling end against the coupling site, dynamic tension-compression force coupling of the coupling element and ossicular chain occur due to surface adhesion which is sufficient for secure mutual connection of the coupling element and the ossicular chain. The coupling element can be provided with an attenuation element which, in the implanted state, adjoins the coupling site and which has entropy-elastic properties, in order to achieve the optimum form of vibration of the footplate of the stapes or of the membrane which closes the round window or an artificial window in the cochlea, in the vestibulum or in the labyrinth, and especially to minimize the risk of damage to the natural structures in the area of the coupling site during and after implantation (see commonly owned, co-pending U.S. patent application Ser. No. 09/626,745).

According to commonly owned co-pending U.S. patent application Ser. No. 09/613,560 the coupling element can be provided with an actuation device for selectively moving the coupling element between an open position, in which the coupling element can engage and disengage the coupling site, and a closed positioning, in which the coupling element, in the implanted state, is connected by force-fit and/or form-fit to the coupling site.

Furthermore, for mechanically coupling the electromechanical transducer 60 to a pre-selected coupling site on the ossicular chain, a coupling arrangement (see commonly owned, co-pending U.S. patent application Ser. No. 09/680,489) is suitable which has a coupling rod which can be caused by the transducer to mechanically vibrate, and a coupling element which can be connected to the pre-selected coupling site. The coupling rod and the coupling element are interconnected by at least one coupling, and at least one section of the coupling element which, in the implanted state, adjoins the coupling site is designed for low-loss delivery of vibrations to the coupling site. A first half of the coupling has an outside contour with at least roughly the shape of a spherical dome which can be accommodated in the inside contour of a second coupling half that is at least partially complementary to the outside contour. The coupling has the capacity to swivel and/or turn reversibly against forces of friction, but is essentially rigid for the dynamic forces which occur in the implanted state. According to a modified embodiment of such a coupling arrangement (see commonly owned, co-pending U.S. patent application Ser. No. 09/680,488) a first half of the coupling has an outside contour with an at least approximately cylindrical, preferably circularly cylindrical, shape which can be accommodated in the inside contour of a second coupling half that is at least partially complementary to the outside contour. A section of the coupling element, which adjoins the coupling site in the implanted state, is designed for low-loss delivery of vibrations to the coupling site in the implanted state. In the implanted state, transmission of dynamic forces between the two halves of the coupling takes place essentially in the direction of the lengthwise axis of the first coupling half. The coupling can be reversibly coupled and decoupled, and can be reversibly moved linearly and/or rotationally with reference to the lengthwise axis of the first coupling half, but is rigid for the dynamic forces which occur in the implanted state.

The fully implantable hearing system shown in FIG. 5 further comprises a sensor (microphone) 14 for airborne sound, which sensor is subcutaneously implantable in the rear wall of the auditory canal, a sensor 15 for body sound, which sensor e.g. may be of the type illustrated in FIG. 4 and which is implantable, separate from the electronic module 18 or 28, in the bony region of the mastoid, a wireless remote control 62 to control the implant functions by the implant wearer, and, when using an implantable secondary battery 42, a transcutaneous charging system comprising a charging device 63 and a charging coil 64 for wireless transcutaneous recharging of the battery 42 (FIG. 3) provided for power supply of the hearing system.

The airborne sound sensor 14 can advantageously be built in the manner known from commonly owned U.S. Pat. No. 5,814,095. Particularly, sensor 14 can be provided with a microphone capsule which is accommodated hermetically sealed on all sides within a housing, and with an electrical feed-through connector for routing at least one electrical connection from within the housing to the outside thereof. The housing has at least two legs which are arranged at an angle relative to one another, a first one of the legs containing the microphone capsule and being provided with a sound inlet membrane, and a second one of the legs containing the electrical feed-through connector and being set back relative to the plane of the sound inlet membrane. The geometry of the microphone housing is chosen such that when the microphone is implanted in the mastoid cavity, the leg which contains the sound inlet membrane projects from the mastoid into an artificial hole in the posterior bony wall of the auditory canal and the sound inlet membrane touches the skin of the wall of the auditory canal. To fix the implanted airborne sound sensor 14, there can preferably be a fixation element of the type known from commonly owned U.S. Pat. No. 5,999,632. This fixation element has a sleeve, a cylindrical housing part of which surrounds the leg which contains the sound inlet membrane, wherein the sleeve is provided with projecting, elastic flange parts which can be placed against the side of the wall of the auditory canal facing the skin of the auditory canal. The fixation element preferably comprises a holding device which, before implantation, maintains the flange parts mentioned above, against the elastic restoration force of the flange parts, in a bent position which allows insertion through the hole of the wall of the auditory canal.

The charging coil 64 which is connected to the output of the charging device 63, in the manner known from commonly owned U.S. Pat. No. 5,279,292 which hereby is incorporated by reference, preferably forms part of a transmitting serial resonant circuit which can be inductively coupled to a receiving serial resonant circuit (not shown). The receiving serial resonant circuit can be part of the implantable electronic module 18 or 28, respectively, (FIGS. 1 and 2) and, according to U.S. Pat. No. 5,279,292, can form a constant current source for the battery 42 (FIG. 3). In this case, the receiving serial resonant circuit is connected in a battery charging circuit which, depending on the respective phase of the charging current flowing in the charging circuit, is closed via one or another branch of a full wave rectifier bridge.

In the arrangement shown in FIG. 5, the electronic module 18 or 28, respectively, is connected via a microphone line 65 to the airborne sound sensor 14. Body sound sensor 15 may be connected to the electronic module 18 or 28, respectively, by separable plug-type connector means indicated at 66 in FIG. 4.

Figure 6:
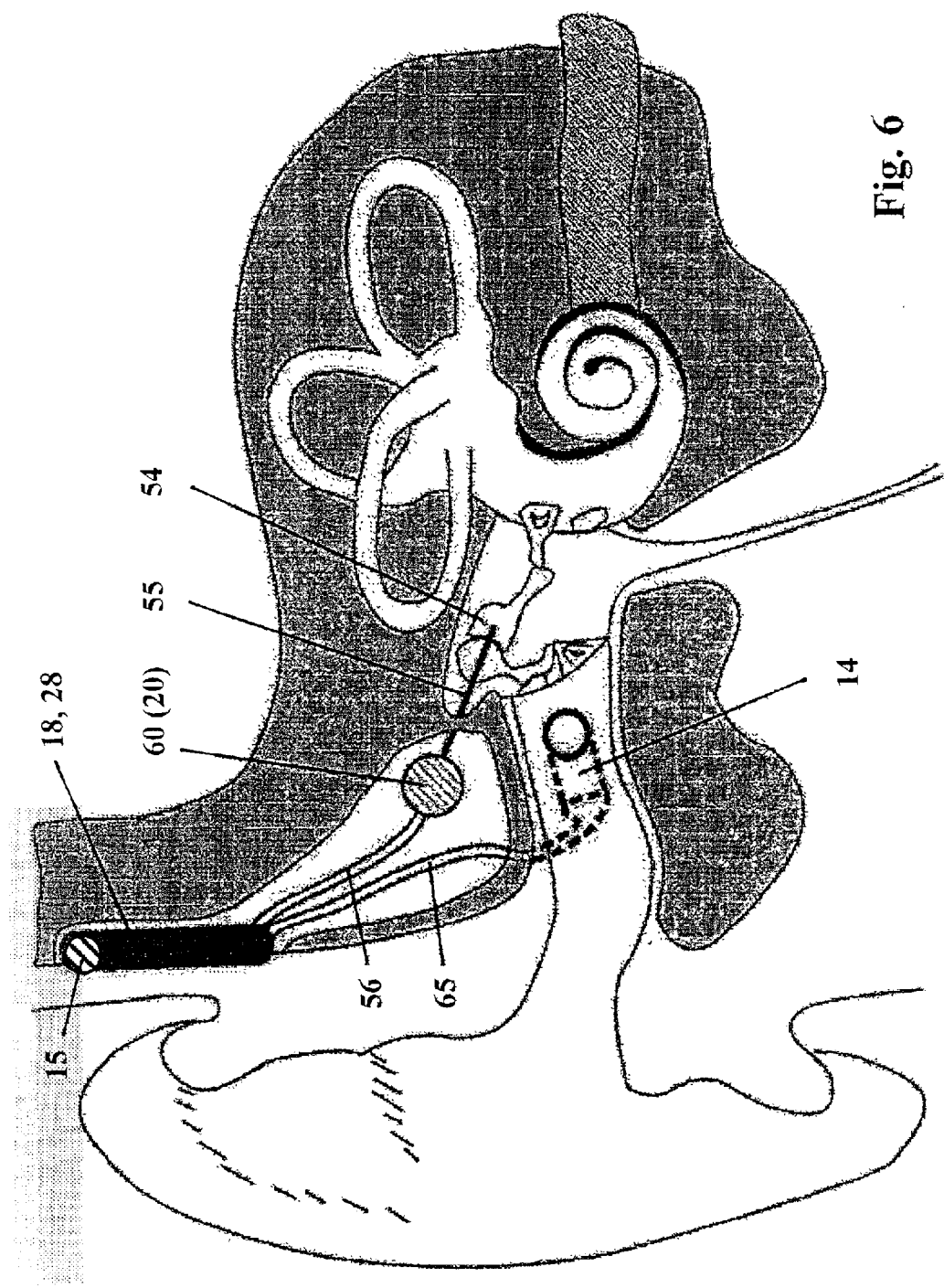

The hearing system shown in FIG. 6 differs from that of FIG. 5 in that the body sound sensor 15 is integrated into the electronic module 18 or 28, respectively, and receives body sound oscillations via a mechanical coupling between the skull and the housing of the electronic module. For this purpose, the internal body sound sensor 15, which for example is structured as shown in FIG. 4, is to be mechanically coupled to the housing of the electronic module.

Figure 7:
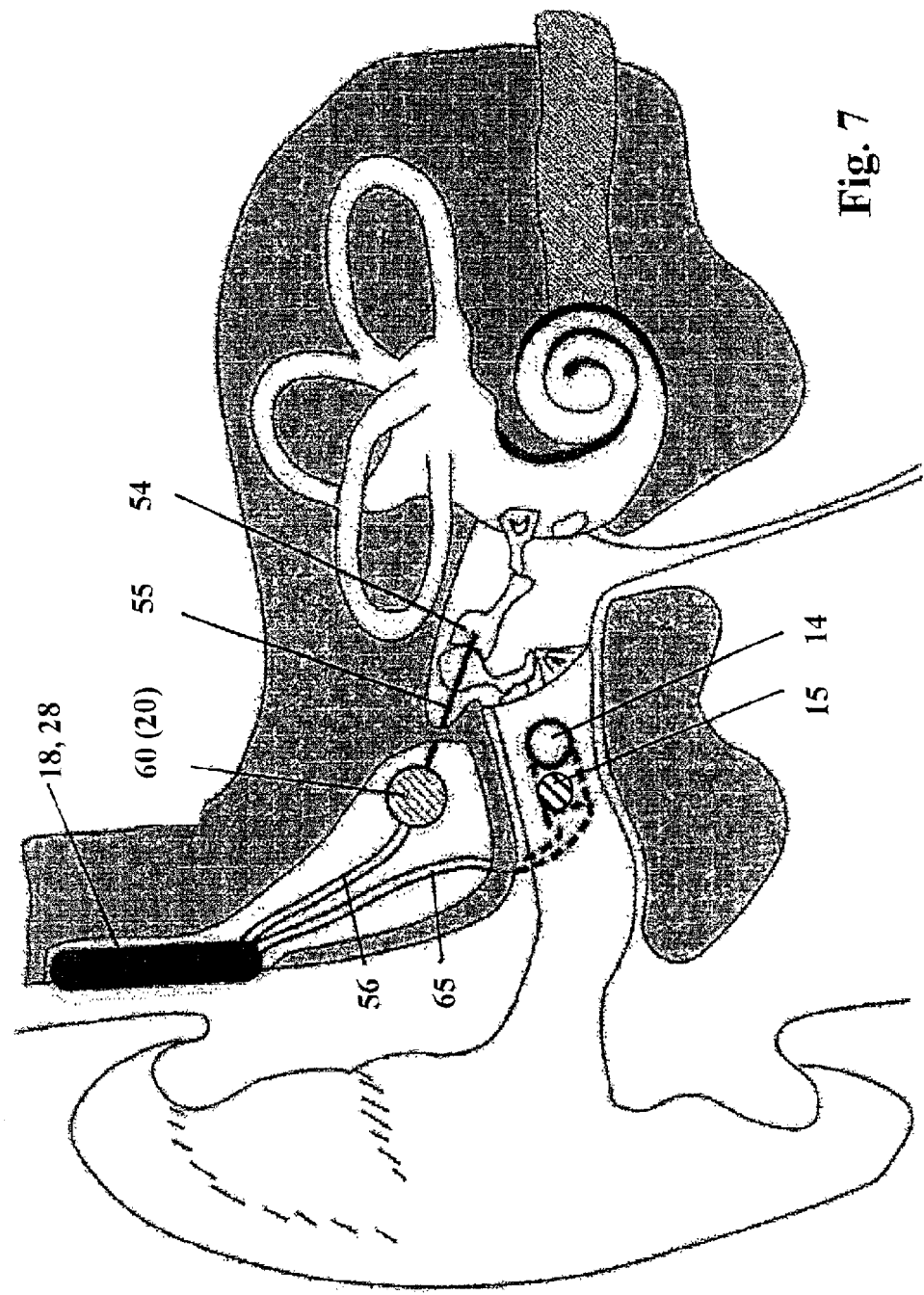

The hearing system shown in FIG. 7 differs from that of FIGS. 5 and 6 in that the body sound sensor 15 is integrated into the housing of the airborne sound sensor 14 which is implanted in the rear wall of the auditory canal. In this embodiment, the body sound sensor 15 is to be mechanically coupled to the microphone housing. In this embodiment, too, the body sound sensor 15 may be designed as shown in FIG. 4, and it is connected to electronic module 18 or 28, respectively, via microphone line 65. When both sensors 14 and 15 have the same ground potential, merely a third conductor is required therefor in line 65.

Figure 8:
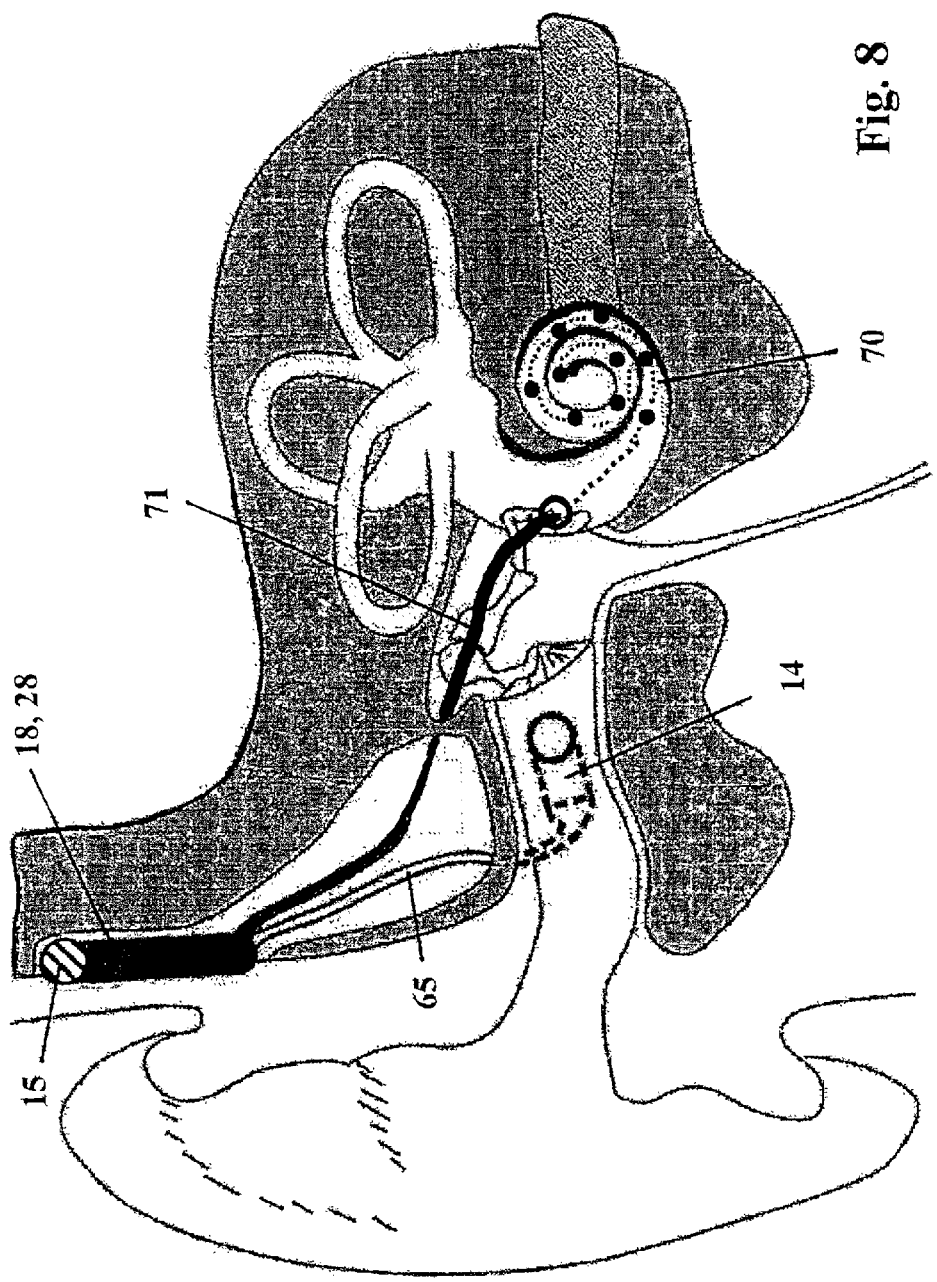
FIG. 8 shows an embodiment of a totally implantable hearing system with multi-channel electrical stimulation of the inner ear via an intracochlear electrode array.

The hearing system of FIG. 8 is designed as an implantable cochlea implant. It differs from the hearing system of FIG. 6 in that, in conformity with commonly owned U.S. Pat. No. 5,814,095, an intracochlear electrode array 70 for a multi-channel electrical excitation of the inner ear is connected, as output actuator (20 in FIGS. 1 to 3), via a line 71 to the electronic module 18 or 28, respectively.

Figure 9:
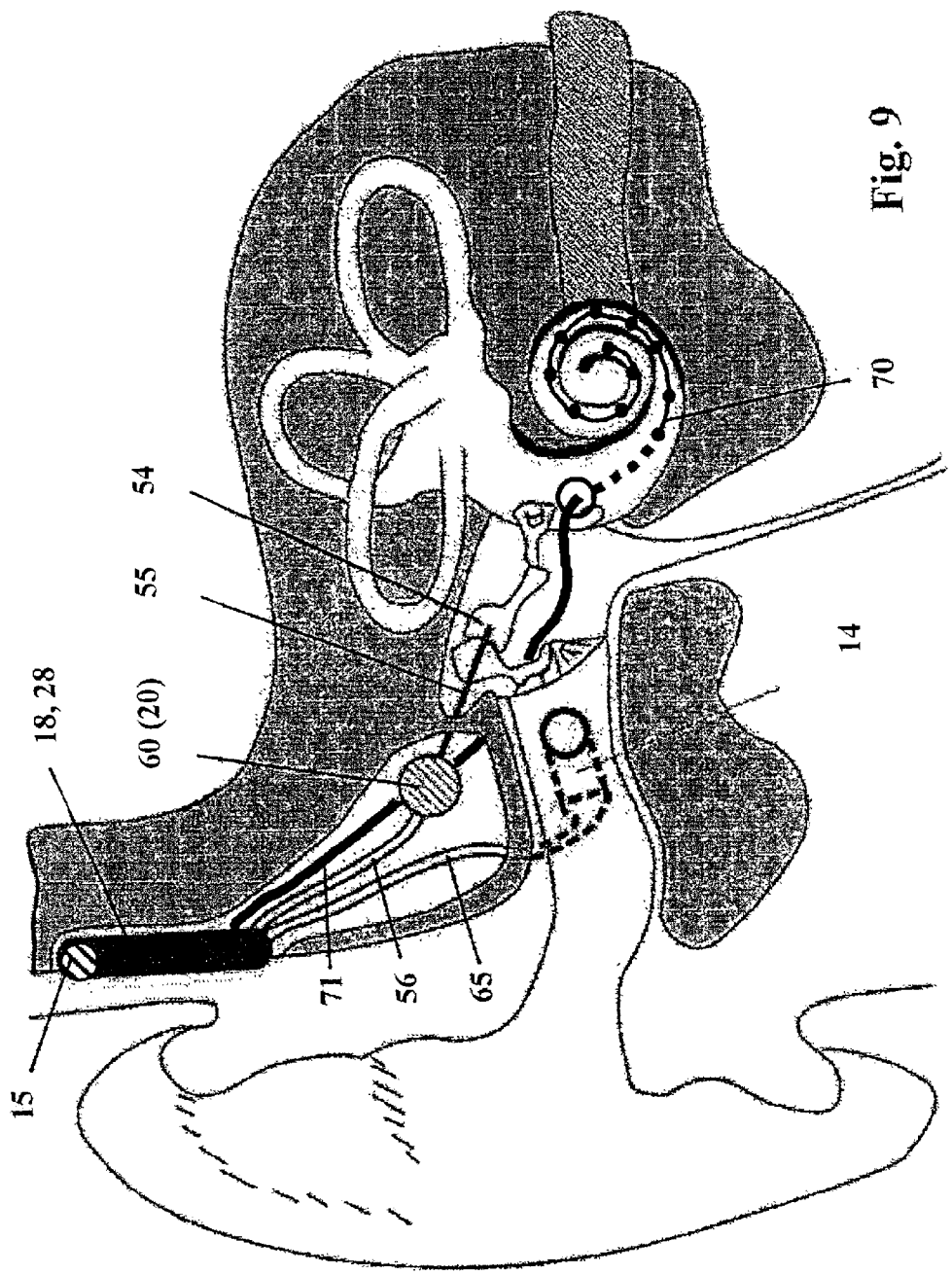
FIG. 9 shows an embodiment of a totally implantable hearing system with combined multi-channel electrical stimulation of the inner ear via an intracochlear electrode array and mechanical stimulation of the middle ear.

The hearing system illustrated in FIG. 9 comprises as output actuators the intracochlear electrode array 70 of FIG. 8 multi-channel electrical excitation of the inner ear in combination with the electromechanical transducer of FIGS. 5 to 7 which provides for a single-channel electromechanical stimulation of the damaged inner ear. Such a combined stimulation is described in more detail in commonly owned U.S. patent application Ser. No. 09/833,642 which hereby is incorporated by reference.

Figure 10:
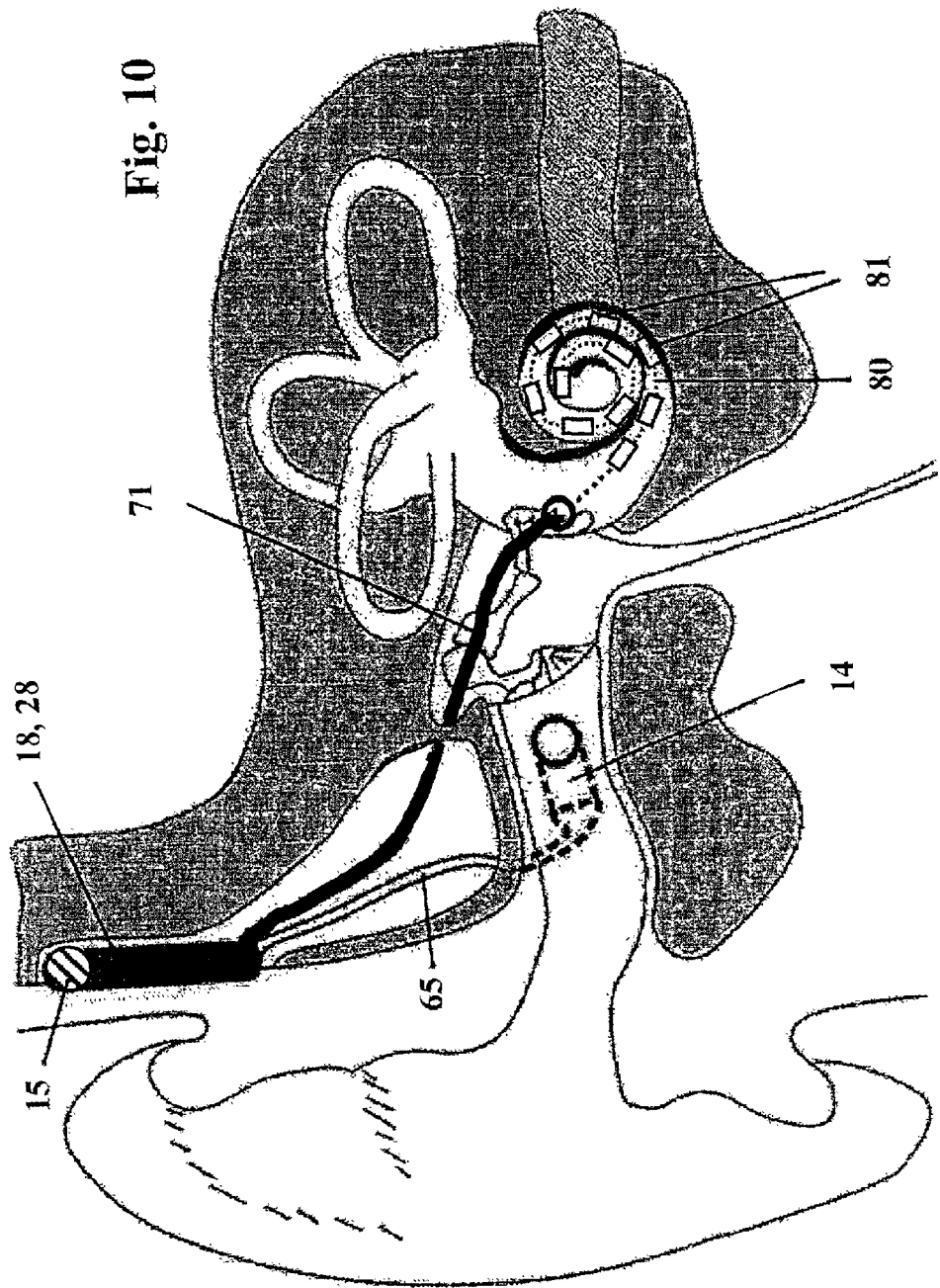
FIG. 10 shows an embodiment of a totally implantable hearing system with multi-channel electromechanical stimulation of the inner ear via an intracochlear transducer array.

The hearing system shown in FIG. 10 differs from the hearing system of FIG. 6 in that the output actuator (20 in FIGS. 1 to 3) is comprised of an extra- or intracochlear transducer array 80 having at least two independent electromechanical transducers 81 which are spaced from each other and which provide for a multi-channel mechanical stimulation. The transducers 81 of transducer array 80 preferably are controlled by the electronic module 18 or 28, respectively, such that locally limited areas of the cochlea are mechanically stimulated in a manner causing a traveling wave configuration to be formed on the basilar membrane of the damaged inner ear, to thereby simulate a "healthy" natural cochlear amplifier. The latter is described in more detail in commonly owned U.S. patent application Ser. No. 09/833,704 which hereby is incorporated by reference.

Figure 11:
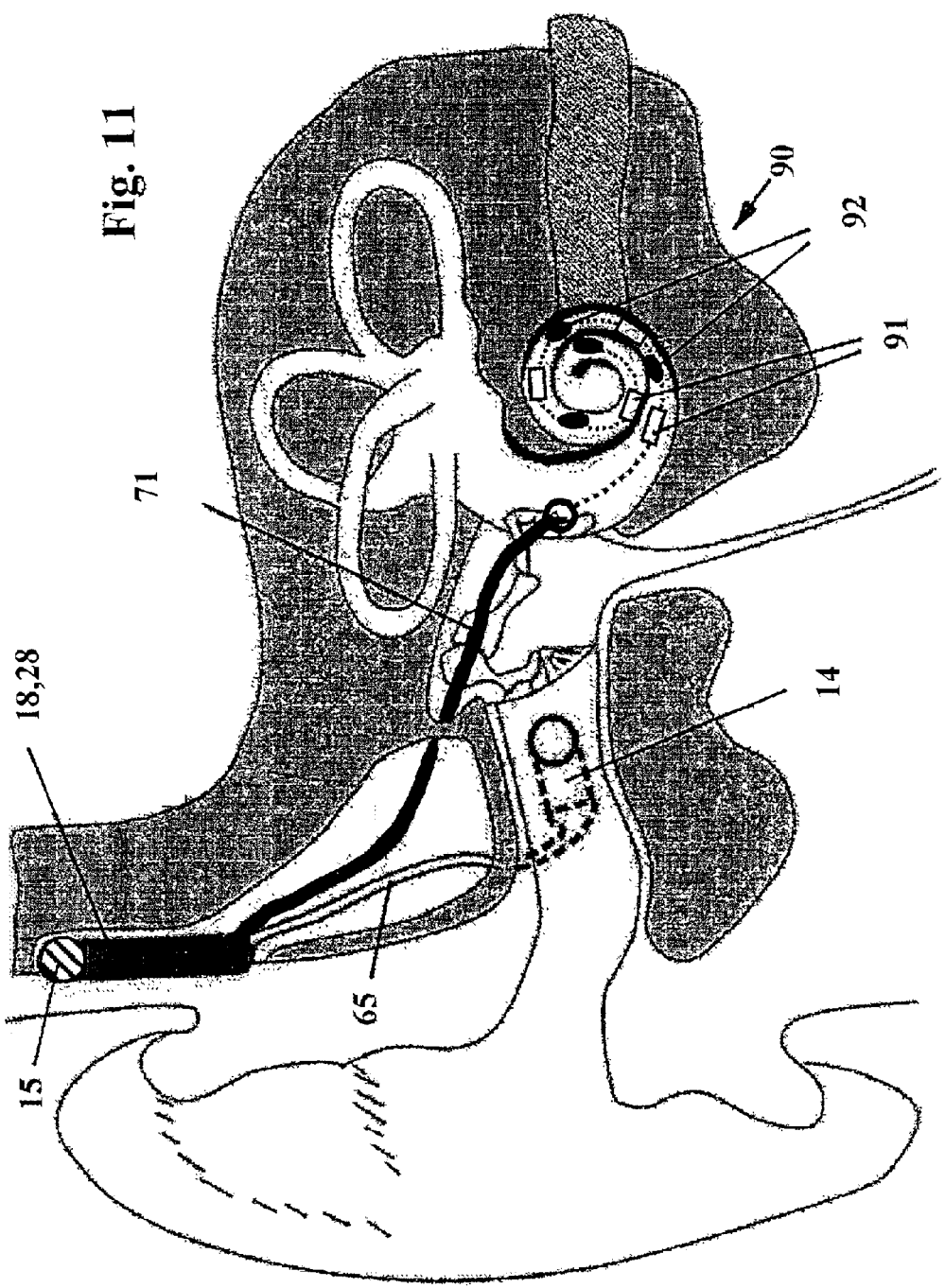
FIG. 11 shows an embodiment of a totally implantable hearing system with direct multi-channel electromechanical and electrical stimulation of the inner ear.

In the hearing system illustrated in FIG. 11 the output actuator (20 in FIGS. 1 to 3) is comprised of an intracochlear array 90 including a series of electromechanical transducers 91 and excitation electrodes 92 for a combined multi-channel electromechanical and electrical stimulation of the inner ear. Details of such an output actuator arrangement are described in commonly owned U.S. patent application Ser. No. 09/833,643 which hereby is incorporated by reference.

It goes without saying that in the hearing systems illustrated in FIGS. 8 to 11 the body sound sensor 15, as described with reference to FIGS. 5 and 7, also can be disposed separately (FIG. 5) or may be disposed together with the airborne sound sensor in a common housing (FIG. 7). When in the hearing system of FIG. 5 the electronic module 18 or 28, respectively, is energized by a primary battery, the charging system including the charging device 63 and the charging coil 64 is omitted. On the other hand, such a charging system also may be provided for in the hearing systems illustrated in FIGS. 6 to 11, when in these hearing systems a secondary battery is used for supplying the implant with energy. Besides, the wireless remote control 62 illustrated in FIG. 5 only, likewise may be used for controlling the hearing systems shown in FIGS. 6 to 11.

Figure 12:
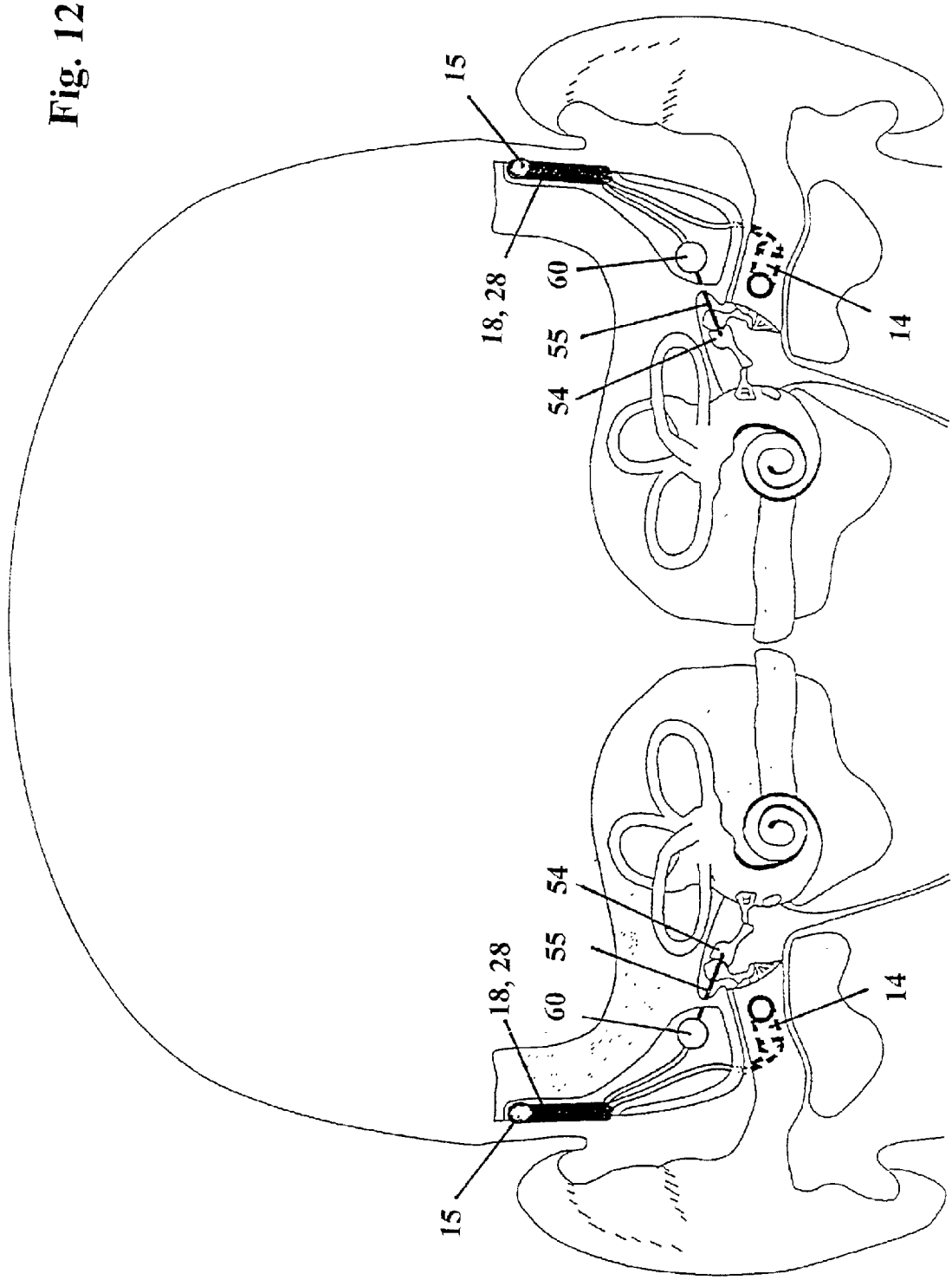
FIG. 12 is a schematic illustration of a binaural hearing system implanted in the head of a bearer.

Furthermore, all the presently described hearing systems may be designed as binaural systems for rehabilitation of a hearing disorder of both ears and correspondingly may be provided with a pair of system units each of which units is associated to one of the two ears. Such a binaural system is shown in FIG. 12. As described in more detail in the aforementioned commonly owned U.S. patent application Ser. No. 09/833,704 both system units may be essentially equal to one another. However, it is also possible that one system unit is a master unit and the other system unit is a slave unit which is controlled by the master unit. The signal processing modules of the two system units may communicate with one another in any desired manner, particularly by a wired implantable line connection or by a wireless connection, preferably a bidirectional high frequency path, a body sound-coupled ultrasonic path or a data transmission path which makes use of the electrical conductivity of the tissue of the implant wearer, for optimizing binaural signal processing and control of the actuators 20, 20' (in the embodiment of FIG. 12 in form of the electromechanical transducer 60) in both system units While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

We claim:

1. A totally implantable hearing system for rehabilitation of hearing disorders, comprising:
   at least one implantable sensor for picking up at least airborne sound and for converting it into electrical airborne sound signals;
   at least one implantable sensor for picking up at least body sound-induced signals and for converting them into electrical body sound signals;
   an electronic module including electronic means for processing and amplification of said airborne sound signals and said body sound signals, said electronic means including means for individually adjusting the ratio of airborne sound signals to body sound signal;
   an output-side actuator arrangement for stimulation of the middle or inner ear; and
   an electrical power supply unit which supplies individual components of the system with energy.

2. The system of claim 1, wherein the at least one body sound sensor is a sensor selected from the group consisting of electromagnetic, electrodynamic, piezoelectric, magnetostrictive or dielectric sensors.

3. The system of claim 2, wherein the at least one body sound sensor is an on-chip semiconductor transducer.

4. The system of claim 1, wherein the at least one body sound sensor comprises a mechanical/electrical transducer which is coupled to an inert mass suspended for oscillating within a sensor housing.

5. The system of claim 1, wherein the at least one body sound sensor has a transmission range from about 100 Hz to about 10 kHz.

6. The system of claim 1, wherein the at least one body sound sensor is tuned to have first mechanical resonant frequency at an upper end of a desired transmission frequency range.

7. The system of claim 1, wherein the at least one body sound sensor is hermetically sealed.

8. The system of claim 1, wherein the at least one body sound sensor is adapted for implantation separate from the electronic module.

9. The system of claim 8, further comprising separable plug-type connector means for connecting the at least one body sound sensor to the electronic module.

10. The system of claim 1, wherein the at least one body sound sensor is integrated into the electronic module.

11. The system of claim 1, further comprising wireless telemetry means for transmission of data between the implanted part of the system and an external unit.

12. The system of claim 11, wherein said telemetry means is adapted for adjusting the ratio of airborne sound signals to body sound signals.

13. The system of claim 1, wherein the system is a binaural system for rehabilitation of a hearing disorder of both ears and has two system units, one each for each of two ears of a wearer, and wherein at least one of said system units is provided with a body sound sensor.

14. The system of claim 1, wherein the at least one airborne sound sensor is designed for picking up a mixture of airborne sound and body sound and for converting it into electrical signals.

15. The system of claim 1, wherein the at least one body sound sensor is designed for picking up substantially body sound only and for converting it into electrical signals.

16. The system of claim 1, comprising amplitude and phase relationship set means for at least one function selected from the group consisting of adjusting the amplitude and phase relationships between the airborne sound signals and the body sound signals, and of programming the amplitude and phase relationships between the airborne sound signals and the body sound signals.

17. The system of claim 16, wherein the electronic means comprise a digital signal processor which contains software modules implementing said amplitude and phase relationship set means.

18. The system of claim 1, comprising units for analog preamplification and subsequent analog electronic processing of the airborne sound signals and the body sound signals.

19. The system of claim 1, comprising units for preamplification and analog-to-digital conversion of the airborne sound signals and the body sound signals.

20. The system of claim 19, wherein the electronic means comprise a digital signal processor for at least one function selected from the group consisting of further processing of the digital data and of generating digital signals for tinnitus masking.

21. The system of claim 20, wherein the electronic means comprise a digital-to-analog converter unit, connected between the digital signal processor and the output-side actuator arrangement, for digital-to-analog conversion of control signals delivered by the signal processor for controlling the output-side actuator arrangement.

22. The system of claim 20, further comprising wireless telemetry means for transmission of data between the signal processor and an external programming system, wherein a rewritable implantable storage arrangement is assigned to the signal processor for storage and retrieval of an operating program, and wherein at least parts of the operating program are adapted to be at least partially replaced by data transmitted from the external programming system via the telemetry means.

23. The system of claim 22, further comprising a buffer storage arrangement in which data transmitted from the external programming system via the telemetry means are buffered before being relayed to the signal processor.

24. The system of claim 23, further comprising a checking logic for checking data stored in the buffer storage arrangement before said data are relayed to the signal processor.

25. The system of claim 24, comprising a microprocessor module for control of at least one of a digital-analog converter, said analog-digital converter, and said signal processing unit, via a data bus; wherein the checking logic and the buffer storage arrangement are implemented in the microprocessor module.

26. The system of claim 23, wherein the buffer storage arrangement comprises at least two storage areas for storage and retrieval of data transferred from the external programming system via the telemetry means.

27. The system of claim 22, comprising a microprocessor module for control of at least one of a digital-analog converter, an analog-digital converter, and said signal processing unit via a data bus, wherein at least one of a plurality of program parts are adapted to be transferred between the external programming system, the microprocessor module and the signal processor via the data bus and the telemetry means.

28. The system of claim 27, wherein an implantable storage arrangement for storage of an operating program for the microprocessor module is assigned to the microprocessor module, and at least one of a plurality of parts of the operating program for the microprocessor module is adapted to be replaced by data transferred from the external programming system via the telemetry means.

29. The system of claim 22, comprising at least two storage areas for storage and retrieval of at least said operating program of the signal processor.

30. The system of claim 22, wherein the telemetry means is adapted for transmission of operating parameters between the implantable part of the system and the external programming system.

31. The system of claim 20, comprising a microprocessor module for control of at least one of a digital-analog converter, said analog-digital converter, and said signal processor, via a data bus.

32. The system of claim 20, wherein a preprogrammed read-only memory area is assigned to the signal processor.

33. The system of claim 20, wherein the digital signal processor contains software modules for controlling spectral, temporal amplitude- and phase-referenced signal properties of the output-side actuator arrangement.

34. The system of claim 33, wherein the software modules are static containing results of scientific findings that are stored in a program storage of the digital signal processor and remain unchanged.

35. The system of claim 33, wherein the software modules are adaptively dynamic.

36. The system of claim 33, wherein the software modules are adaptive for parameter matching by implant wearer training.

37. The system of claim 20, wherein the digital signal processor contains software modules for tinnitus masking cocurrent with hearing device operation of the system.

38. The system of claim 20, wherein the digital signal processor contains a software module for optimized approximation of stimulation via an adaptive neural network.

39. The system of claim 38, wherein the neural network is adaptable to training by the implant wearer.

40. The system of claim 1, wherein said output-side actuator arrangement comprises at least one electromechanical transducer for mechanical stimulation of one of the middle ear and the inner ear.

41. The system of claim 1, wherein said output-side actuator arrangement comprises intracochlear stimulation electrodes for electrical stimulation of the inner ear.

42. The system of claim 1, wherein said output-side actuator arrangement comprises a combination of at least one electromechanical transducer for mechanical stimulation of one of the middle ear and the inner ear, and of intracochlear stimulation electrodes for electrical stimulation of the inner ear.

43. The system of claim 1, wherein the electrical power supply unit comprises an implantable rechargeable energy storage element adapted for wireless transcutaneous charging by an external charging device.

* * * * *